(12) United States Patent
Van Der Putten

(10) Patent No.: US 6,504,080 B1
(45) Date of Patent: Jan. 7, 2003

(54) TRANSGENIC ANIMAL MODEL FOR NEURODEGENERATIVE DISORDERS

(75) Inventor: Petrus Herman Maria Van Der Putten, Binningen (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/687,731

(22) Filed: Oct. 13, 2000

(30) Foreign Application Priority Data

Oct. 15, 1999 (GB) ............................................. 9924513

(51) Int. Cl.[7] ...................... A01K 67/027; G01N 33/00; C12N 15/00; C12N 5/00; C12N 15/63
(52) U.S. Cl. ................................. 800/18; 800/3; 800/9; 800/12; 800/21; 800/22; 800/25; 435/325; 435/455; 435/463; 435/320.1
(58) Field of Search .................................. 435/455, 463, 435/320.1, 325; 800/18, 21, 22, 25, 3

(56) References Cited

U.S. PATENT DOCUMENTS 6,184,351 B1 * 2/2001 Biere et al. .................. 530/350

FOREIGN PATENT DOCUMENTS

| EP | 0 908 727 | 4/1999 |
|---|---|---|
| WO | WO 95/06407 | 3/1995 |
| WO | WO 00/18917 | 4/2000 |

OTHER PUBLICATIONS

Wall; Transgenic:Livestock: Progress and Prospects for the Future, 1996, Theriogenology 45: 57–68.*

Mullins et. al.; Perspecrives Series: Molecular in Genetically Engineered Animals, 1996, J. Clin. Invest.: S37–S40.*

Moreadith et. al.; Gene targeting in embryonic stem cells: the new physiology and metabolism, 1996, J. Mol. Med. 75: 208–216.*

Masliah et al., Science, vol. 287, "Dopaminergic Loss and Inclusion Body Formation in alpha–Synuclein Mice: Implications for Neurodegenerative Disorders", pp. 1265–1269 (2000).

Goldberg et al., Society for Neuroscience Abstracts, vol. 24(1–2), "Studies of Wild–type and Mutant Alpha–synuclein in Transgenic Mice," pp. 966 (1998).

Jakes et al., FEBS Letters, vol. 345, "Identification of Two Distinct Synucleins from Human Brain," pp. 27–32 (1994).

* cited by examiner

*Primary Examiner*—Deborah Crouch
*Assistant Examiner*—Thaian N. Ton
(74) *Attorney, Agent, or Firm*—Susan Hess

(57) ABSTRACT

Animal model useful for testing potential therapeutic agents for the treatment of neurodegenerative disorders, in particular disorders associated with the presence of Lewy pathology.

17 Claims, No Drawings

SEQUENCE LISTING

<160> NUMBER OF SEQ ID NOS: 12

<210> SEQ ID NO 1
<211> LENGTH: 24

```
<212> TYPE: DNA
<213> ORGANISM: Artificial Sequence
<220> FEATURE:
<223> OTHER INFORMATION: Description of Artificial Sequence: primer

<400> SEQUENCE: 1
cgacgacagt gtggtgtaaa ggaa                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 2
tgggcacatt ggaactgagc actt                                          24

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 3
agtggtgcat ggtgtgacaa cagtggctga ga                                 32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 4
tctcagccac tgttgtcaca ccatgcacca ct                                 32

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 5
gaagggtatc aagactacga acc                                           23

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 6
caagctctaa tacgactcac tataggcaca ttggaactga gcact                   45

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 7
```
agggctgtgg agacagaact cg                                          22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 8
tgggcacatt ggaactgagc actt                                        24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 9
gggagccgtg tggagcaaaa atac                                        24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 10
tgggcacatt ggaactgagc actt                                        24

<210> SEQ ID NO 11
<211> LENGTH: 9168
<212> TYPE: DNA
<213> ORGANISM: Artificial Sequence
<220> FEATURE:
<223> OTHER INFORMATION: Description of Artificial Sequence:DNA-construct

<400> SEQUENCE: 11
aatcaaaggt gtgagctctg taggtcttaa gttccagaag aaagtaatga agtcacccag     60
cagggaggtg ctcagggaca gcacagacac acacccagga cataggctcc cacttccttg    120
gctttctctg agtggcaaag gaccttaggc agtgtcactc cctaagagaa ggggataaag    180 agagggctg aggtattcat catgtgctcc gtggatctca agccctcaag gtaaatgggg     240
acccacctgt cctaccagct ggctgacctg tagctttccc caccacagaa tccaagtcgg    300
aactcttggc acctagagga tctcgaggtc cttcctctgc agaggtcttg cttctcccgg    360
tcagctgact ccctccccaa gtccttcaaa tatctcagaa catggggaga aacggggacc    420
ttgtccctcc taaggaaccc cagtgctgca tgccatcatc ccccccaccc tcgccccac    480 ccccgccact tctccctcca tgcataccac tagctgtcat tttgtactct gtatttattc    540
cagggctgct tctgattatt tagtttgttc tttccctgga gacctgttag aacataaggg    600
cgtatggtgg gtaggggagg caggatatca gtccctgggg cgagttcctc cctgccaacc    660
aagccagatg cctgaaagag atatggatga gggaagttgg actgtgcctg tacctggtac    720
agtcatactc tgttgaaaga atcatcgggg aggggggggg gctcaagagg ggagagctct    780
gctgagcctt tgtggaccat ccaatgagga tgagggctta gattctacca ggtcattctc    840
agccaccaca cacaagcgct ctgccatcac tgaagaagcc ccctagggct cttgggccag    900
ggcacactca gtaaagatgc aggttcagtc agggaatgat ggggaaaggg gtaggaggtg    960

```
ggggagggat caccccccctc ctctaaaaca cgagcctgct gtctccaaag gcctctgcct    1020
gtagtgaggg tggcagaaga agacaaggag ccagaactct gactccagga tctaagtccg    1080
tgcaggaagg ggatcctaga accatctggt tggacccagc ttaccaaggg agagccttta    1140
ttcttctttc ccttgcccct ctgtgccagc ccctcttgct gtccctgatc ccccagacag    1200
cgagagtctt gcaacctgcc tcttccaaga cctcctaatc tcaggggcag gcggtggagt    1260
gagatccggc gtgcacactt tttggaagat agctttccca aggatcctct cccccactgg    1320
cagctctgcc tgtcccatca ccatgtataa taccaccact gctacagcat ctcaccgagg    1380
aaagaaaact gcacaataaa accaagcctc tggagtgtgt cctggtgtct gtctcttctg    1440
tgtcctggcg tctgtctctt ctgtgttctt ccaaggtcag aaacaaaaac cacacacttc    1500
aacctggatg gctcggctga gcacttctgt gtgcagaagg tccaaccaga ctctggggta    1560
ccccggccct ccctattccc ttgcctcctg tctcccgctt tttatagctc cctatgctgg    1620
gcttctctgg agagtgaaat ctttgcccaa atcaatgcgc attctctctg ctgagtcatc    1680
tggcgacagc agttgagttc acccgccaac acatgggccc agctatgtag ccgaaccctg    1740
gctctggaag tgccagggac tttgtgcata agtatgtacc atgcccttt   ttcacagtcc    1800 tagctctgca gaagtgcagc ctgaaggcct gtctgctgag aggacatgcc ctggagccct    1860
gaaacaggca cagtgggagg aggaacggag gatgacaggc atcaggccct cagtccaaaa    1920
gcaaccactt gagaatgggc tggagtacga acatgggggt cccgtccctg atccctcct    1980 caaagagtaa taagtaaaat ataaacaggt accccaggcc gttctgggtt tgggttgtaa    2040
tgggatccat ttgcagagaa ctattgagac agccagccg tactgtgaca ggcaatgtgg    2100
gggaggaggt tgaatcactt ggtatttagc atgaatagaa taattccctg aacatttttc    2160
ttaaacatcc atatctaaat taccaccact cgctcccagt cttcctgcct ttgcgccagc    2220
ctcctgtctg gccatgcctg aagaaggctg gagaagccac ccacctcagg ccatgacact    2280
gccagccact tggcaggtgc agccaaacct gagctgtccc agaaagggac attctcaaga    2340
cccaggcacc ctgatcagca ctgacttgga gctacaagtg tcatgccaga aaagtctcta    2400
agaaaacctt ttcagggaaa aggggtgac tcaacaccgg gcaagtttgg gaagccccac    2460
ccttcgagtg atggaagagc agataggaag cctcagaaga gagacaccgg cacccaggta    2520
acgttcctca tgtggtctct gtcacactag gtgctcttcc ctggacatct ccgtgaccac    2580
actctcagtt cttagggaga tgcgggtgct ctctgaggct atctcagagt tgcagattct    2640
gaggcctaga gtgactacag tcagcctagg aagccacaga ggactgtgga ccaggagggc    2700
agaagaggag aagggaagaa aaaccatcag ataggacttg caatgaaact aacccaagac    2760
aatcataatg cagacaggaa tgttaaaggc gttcagcagc tggccatgac acccatctgt    2820
ccctctggcc aagtcagcaa gcctggaaga cctgggactc ctgcccatat gtcctaagct    2880
ccccacccac ccactcgttc actgtcctta ttctctctct accttcagcc acttagtttc    2940
ctaccttaag tcctagaatt gatcctggcg taatagcgaa gaggcccgca ccgatcgaat    3000
tcttagcggc cgctaatcgc ccttcccaac agttgcgcag cctgaatggc gaatggcgcc    3060
tgatgcggta ttttctcctt acgcatctgt gcggtatttc acaccgcata tggtgcactc    3120
tcagtacaat ctgctctgat gccgcatagt taagccagcc ccgacacccg ccaacacccg    3180
ctgacgcgcc ctgacgggct tgtctgctcc cggcatccgc ttacagacaa gctgtgaccg    3240
tctccgggag ctgcatgtgt cagaggtttt caccgtcatc accgaaacgc gcgagacgaa    3300
```

-continued

```
agggcctcgt gatacgccta tttttatagg ttaatgtcat gataataatg gtttcttaga     3360
cgtcaggtgg cacttttcgg ggaaatgtgc gcggaacccc tatttgttta tttttctaaa     3420
tacattcaaa tatgtatccg ctcatgagac aataaccctg ataaatgctt caataatatt     3480
gaaaaaggaa gagtatgagt attcaacatt tccgtgtcgc ccttattccc ttttttgcgg     3540
cattttgcct tcctgttttt gctcacccag aaacgctggt gaaagtaaaa gatgctgaag     3600
atcagttggg tgcacgagtg ggttacatcg aactggatct caacagcggt aagatccttg     3660
agagttttcg ccccgaagaa cgttttccaa tgatgagcac ttttaaagtt ctgctatgtg     3720
gcgcggtatt atcccgtatt gacgccgggc aagagcaact cggtcgccgc atacactatt     3780
ctcagaatga cttggttgag tactcaccag tcacagaaaa gcatcttacg gatggcatga     3840
cagtaagaga attatgcagt gctgccataa ccatgagtga taacactgcg gccaacttac     3900
ttctgacaac gatcggagga ccgaaggagc taaccgcttt tttgcacaac atgggggatc     3960
atgtaactcg ccttgatcgt tgggaaccgg agctgaatga agccatacca aacgacgagc     4020
gtgacaccac gatgcctgta gcaatggcaa caacgttgcg caaactatta actggcgaac     4080
tacttactct agcttcccgg caacaattaa tagactggat ggaggcggat aaagttgcag     4140
gaccacttct gcgctcggcc cttccggctg gctggtttat tgctgataaa tctggagccg     4200
gtgagcgtgg gtctcgcggt atcattgcag cactggggcc agatggtaag ccctcccgta     4260
tcgtagttat ctacacgacg gggagtcagg caactatgga tgaacgaaat agacagatcg     4320
ctgagatagg tgcctcactg attaagcatt ggtaactgtc agaccaagtt tactcatata     4380
tactttagat tgatttaaaa cttcatttt aatttaaaag gatctaggtg aagatccttt     4440
ttgataatct catgaccaaa atcccttaac gtgagttttc gttccactga gcgtcagacc     4500
ccgtagaaaa gatcaaagga tcttcttgag atcctttttt tctgcgcgta atctgctgct     4560
tgcaaacaaa aaaaccaccg ctaccagcgg tggtttgttt gccggatcaa gagctaccaa     4620 ctcttttcc gaaggtaact ggcttcagca gagcgcagat accaaatact gttcttctag     4680
tgtagccgta gttaggccac cacttcaaga actctgtagc accgcctaca tacctcgctc     4740
tgctaatcct gttaccagtg gctgctgcca gtggcgataa gtcgtgtctt accgggttgg     4800
actcaagacg atagttaccg gataaggcgc agcggtcggg ctgaacgggg gttcgtgca     4860 cacagcccag cttggagcga acgacctaca ccgaactgag atacctacag cgtgagctat     4920
gagaaagcgc cacgcttccc gaagggagaa aggcggacag gtatccggta agcggcaggg     4980
tcggaacagg agagcgcacg agggagcttc caggggggaaa cgcctggtat ctttatagtc     5040
ctgtcgggtt tcgccacctc tgacttgagc gtcgattttt gtgatgctcg tcagggggc     5100 ggagcctatg gaaaaacgcc agcaacgcgg cctttttacg gttcctggcc ttttgctggc     5160
cttttgctca catgttcttt cctgcgttat cccctgattc tgtggataac cgtattaccg     5220
cctttgagtg agctgatacc gctcgccgca gccgaacgac cgagcgcagc gagtcagtga     5280
gcgaggaagc ggaagagcgc ccaatacgca aaccgcctct ccccgcgcgt tggccgattc     5340
attaatgcag gatcgcggcc gcgatcccg ggcgagctcg aattcagaga ccgggaacca     5400
aactagcctt taaaaacat aagtacagga gccagcaaga tggctcagtg ggtaaaggtg     5460
cctaccagca agcctgacag cctgagttca gtccccacga actacgtggt aggagaggac     5520
caaccaactc tggaaatctg ttctgcaaac acatgctcac acacacacac acaaatagta     5580
taaacaattt taaatttcat ttaaaaataa tttgtaaaca aaatcattag cacaggtttt     5640
agaaagagcc tcttggtgac atcaagttga tgctgtagat ggggtatcat tcctgaggac     5700
```

-continued

```
ccaaaaccgg gtctcagcct ttccccattc tgagagttct ctcttttctc agccactagc    5760
ttgaagagta gagtggctca gcactgggct cttgagttcc caagtcctac aactggtcag    5820
ctgactacta accagccatg aagaaacaag gagtggatgg gctgagtctg ctgggatggg    5880
agtggagtta gtaagtggcc atggatgtaa tgacccagca atgctggcta gaaggcatgc    5940
ctcctttcct tgtctggaga cggaacggga gggatcatct tgtactcaca gaaggagaa     6000 cattctagct ggttgggcca aaatgtgcaa gttcacctgg agtggtggt gcatgctttt     6060 aactccagta ctcaggaggc agggccaggt ggatctctgt gagttcaaga ccagccctgc    6120
actatggaga gagttttggg acagccagag ttacacagaa aaatcctggt ggaaaatctg    6180
aaagaaagag agaagaaag aaagaaagaa aggaagaaag aaagaaagag tggcaggcag     6240
gcaggcagga ggaaggaagg aaggaaggaa ggaaggaagg aaggaaggaa ggaaaatagg    6300
tgcgacttca agatccggag ttacaagcag aatgcactgt ttccctaaca gggccaagtg    6360
ttttgagtaa ctgaaggtgg gcatgatgcc tgggaagcag aaacaagcca ggcagatgca    6420 cccccttgcct tgcttccgaa gggctgcagt agcatggaaa acatggaaaa caaccaatcc   6480 attcccttg ctgatataac aggctccaaa gccaaaacct gtcactggag gctcaagagc    6540
agatctccag ccaagaggca aaggaatggg ggaagctgga gggcctccct ctggttatcc    6600
aggcttctga aggttcaagc aaagaaaggg ttacaacctt aaaaggagag cgtcccgggg    6660
tatgggtaga agactgctcc accccgaccc ccagggtccc taaccgtctt ttccctgggc    6720
gagtcagccc aatcacagga ctgagagtgc ctctttagta gcagcaagcc acttcggaca    6780
cccaaatgga acacctccag tcagccctcg ccgaccaccc cacccctcc atccttttcc     6840 ctcagcctcc gattggctga atctagagtc cctccctgct cccccctctc tccccacccc    6900
tggtgaaaac tgcgggcttc agcgctgggt gcagcaactg gaggcgttgg cgcaccagga    6960
ggaggctgca gctaggggag tccaggtgag agcaggccga cgggagggac ccgcacatgc    7020
aaggaccgcc gcaggcgag gatgcaagcc ttccccagct acagttttgg gaaaggatac      7080
cagggcgctc ctatatgggg gcgcgggaac tggggaaaga aggtgctccc aggtcgaggt    7140
gggagaggaa ggcagtgcgg ggtcacgggc tttctccctg cgctaaccga cgcatttcga    7200
agagtgggtg ccggaggaga ccatgaggaa ggacatcaag gacagccttt ggtccccaag    7260
ctcaaatcgc tttagtggtg cgaatagagg gaggaggtgg gtggcaaact ggagggagtc    7320
cccagcgggt gacctcgtgg ctggctgggt gcggggcacc gcaggtaaga aaaccgcaat    7380
gttgcgggag gggactgggt ggcaggcgcg gggaggggga aagctagaaa ggatgcgagg    7440
gagcggaggg gggagggagc gggagaatct caactggtag aggaagatta aaatgaggaa    7500
atagcatcag ggtggggtta gccaagccgg gcctcaggga aagggcgcaa agtttgtctg    7560
ggtgtgggct taggtgggct gggtatgaga ttcggggcgc cgaaaacact gctgcgcctc    7620
tgccaaatca cgctacccct gtatctagtt ctgccaggct tctccagccc cagccccaat    7680
tcttttctct agtgttcccc cttccctccc ctgaatctca gcccacact ccctcctcca     7740 taacccactg ttatcaaatc taagtcattt gccacccaac aaccatcagg aggcggaagc    7800
agacgggagg agtttgagat caacttgggc tacatcacga gttccaggct caccaaggct    7860
tcttaaggag accttgtctc taaaattaat taattaatta attaatagtc ccctttctct    7920
gccacagaac cttgggatct ggctcctggt cgcagctccc cccaccccag gctgacattc    7980
actgccatag cccatccgga aatcctagtc tatttcccca tggatcttga actgcagaga    8040
```

```
gaatggcaga gtggcccgcc ctgtgcaaag gatgttccta gcctaggtgg agctcgcgaa    8100
ctcgcagact gtgcctctct tgggcaagga caggctagac agcctgccgg tgtgttgagc    8160
tagggcactg tggggaaggc agagaacctg tgcagggcag caatgaacac aggaccagaa    8220
aactgcagcc ctaggaacac tcaagagctg gccatttgca agcatctctg gcctccgtgc    8280
ttctcactca tgtcccatgt cttatacagg cctctgtggc acctcgcttg cctgatctca    8340
tccctagccg ttaagctttc tgcatgactt atcacttggg gcataatgct ggatacctac    8400
cattttctta gacccatca aaatcctatt tgagtgtacg gttcggagaa cctcattat     8460 ccggtaaatg tcttttactc tgctctcagg gagctgaggc aggacatcct gagatacatt    8520
gggagaggag atacagtttc aataaaataa taggttgggt ggaggtacat gcctataatg    8580
ccaccactca ggaaatggtg gcagcttcgt gagtttgagg ccaacccaag aaacatagtg    8640
aaaccctgtc agtaaataag taagcaagta tttgagtatc tactatatgc tagggctgac    8700
ctggacatta ggggtcatct tctgaacaaa ctagtgcttg agggaggtat ttgggggtttt    8760 tgtttgttta atggatctga atgagttcca gagactggct acacagcgat atgactgagc    8820
ttaacacccc taaagcatac agtcagacca attagacaat aaaaggtatg tatagcttac    8880
caaataaaaa aattgtattt tcaagagagt gtctgtctgt gtagccctgg ctgttcttga    8940
actcactctg tagaccaggc tggcctggaa atccatctgc ctgcctctgc ctctctgcct    9000
ctctgcctct ctgcctctct ctctgcctct ctctgccct ctctgcccct                 9060 ctctgccct ctctgccgcc tctgccttt gccctctgcc ctctgttctc tggcctctgc    9120
cctctgccct ctggcctctg gcctctgcct ctgcctcttg agtgctgg                  9168

<210> SEQ ID NO 12
<211> LENGTH: 8815
<212> TYPE: DNA
<213> ORGANISM: Artificial Sequence
<220> FEATURE:
<223> OTHER INFORMATION: Description of Artificial Sequence:
      DNA-construct

<400> SEQUENCE: 12
gcggccgccg gcctcgaggg ccggatctgc aggtcgacca gctggccaag cttgcatgcc      60
tgcaggtcga cctgcaggtc aacggatcgt gggattgggt ccctggggaa aggtgttgcc     120
cgtggggtca gactgagcca taagcggctg tagccttggg aatgacatac ttccaagttc     180
tcactaggaa cccggagtag gggcagcccc gtggagaaag cctggctgtc ccggccctca     240
ctgcgagatt actcacccctt gtgtcctccc ttgttctctc acttctacaa aacctgaccc     300
ttgctcaaat ggcagtgaga agctgctggg tgggaactgt tgctaccatc tgcatgggct     360
ctggggatga ggtggccaca gcagcagctg tcatgcttgt taaacacaag gttccttcac     420
cccataatgg ggctggtgac attgtcctaa acagaagggc tttgccaagt agaaggatta     480
ttgttgggta aataagagcc ctaaaggtgg agtttttgtc ttccaggaac cttctttaaa     540
tcactaggaa ctgcccttag gtcaactgtc tcggataagt gcatctagtt ttagatcagt     600
ccaaacagcc tctatcagtt caaagacccc tacataaagt ctgttgctct tccaccatgc     660
cccctccacc tctgagatag ccttggcagt ttaatctccg ataaaccttt ctttcaactc     720
acggcatgtt cgtgtttggt gggatcactg tggcctcaca gtagaggatg tccagagctg     780
tgtttggctc tgtcccttga cgttcctctc ccttgtattc gttttgtttt gttttgtttt     840 ttgttttttaa tcaacccaac acaaactaga gtcttcttga aagagggaac cttaattgat    900
```

-continued

```
aaaatgccat ctccaggcct aggaagatga ctcaacagtt aagagcactg gccacttttc    960
cacaggtctt gggtttgatt cccagtcccc acatggtggc tcacaaccag ttctagtgga   1020
tccaactccc tcttctggct tctgcggaca ccagacatac aattggtatg tggacacatg   1080
taggcaagac attcacatac attgaaaaca aaaagcctgt tgagagaaaa tatctccatc   1140
agatttacct agaagcaaat ctgtatgcat tttcttgctt aatggttggt atgagagggc   1200
ccagcccact gtgggtggta accataggct ggtgatcctg gggtgcatag aaaggcaagt   1260
tgggaaaggc actttgcaat gtcccttcat agtctcagct taagtccctg cctccaggct   1320
cccaccctga cttttcccag tgatggacag tgaccaggac atgtaagcca ataaactct    1380 ctccttccca gtgacttttt ggtcctggtg tttattacag caacagaaat caagctagga   1440
cattgctttt cttttactt catatacttc gatcatgtgt gtttgtatgt gattagcagt    1500
atggaagcca aggacagac tagaatattg gttctttgat gcattgggag aatttccttc    1560 ctggggcta ggaggagcat ggaggagcag agactggaca cactttggc ctaccaattg     1620 tagcccttcc ctaagacatc aaggccaact gcaatcaggg cagaccatca tacagcatgt   1680
ggggaggaag gattgagtac ttcaatgagg gtcccatgac tctatcccct ccatccatgc   1740
tgggcggtca tcagtcaaca agccaagctg agaaatcctc tgcaggctta actcaagcga   1800
agtcatgaag tcaagatatt gattgtttgg cttggagaat agtgctatgt aacagccgag   1860
tccaccttgc cttgagacca tatcccacac tggcctggag ctcgccaggt aggctacact   1920
gcttttagct gagtcctagg gatcctcctg cctctgcctc ctcactgctg ggattagaaa   1980
catgcaccac cacacctgtc tacatgtctt ctaggaatca gactaggccc atatgctgtg   2040
taaaaagaac tctgtggact gagttacctc tgtacactac agagcaagta tttaactggg   2100
ggctggctta caatttcaga ggcttagtcc attacaataa gggcagggag catagcagtg   2160
tgcagaatct gagagctaca tcctgatctg gagagagaaa gagagagaga aagagagaga   2220
gagagagaca gacagacaga cagacagaca gacagacaga cagacactga acctggcatg   2280
gacttttaaa accccaataa catgcccact ccagccaggc cacacccact ctgacaaggc   2340
cacagttcct aacacttctc aaatagtgcc actcctcagt gactaagcat tcaaacacag   2400
cagccacact aggtaactat gaggccgcaa agccacggga tgggagccct ctccacctgg   2460
agaagcctac cctaatgaca gaggtgatag ggttatttct cctgagttcc ccagactgga   2520 ccccaaaca cattaaagtc tgctctaaac caagccaagc tgcccctggg cctcccctgc    2580
caatgtcctc cacacatgca gaagctacac ctcctttgga catctcttca gttcagggg   2640 acaaagctcc agagtctgct gctgtcccat ctcctgtccc tgcccatagg catcctccat   2700
aggcagggcc ctaggaagtt tttctactgt ggcttggcac atgtgaggca agtgagactg   2760
taagactatc cctgctaaat gctggggcca ctgtaactct gctaacacag ccccgggcca   2820
tgctgtgggg agcagaagcc accttgtaga tgagaagaga ggactacaca ccaccacaaa   2880
ctgcaagaaa gaaagcactc ccattcggag caggaaccac tgccctccct accacaggat   2940
gggaggggga ccaccaccca caggctccag tgcttccgtg ggcctgggt gggtaggcag    3000 ccgtcttgca attagacatg attgctgtca catcaccacc gtggtccttg tgagtgacta   3060
atgggaactg aatgtcactc ttattgcttt tactggctaa tttgtcagac tgtcaagtac   3120
tctgggaggt ggcacggagg gtattacgtg actcactggt gcacaggttg gaagaggcaa   3180
gggccttagg ggggacagag ggaagcagga ataccagaga ggaccagggg tctgacccat   3240
gacattttcg gaaagtctga ggggcatggg agctgaggtt accccacctg tcacatatcg   3300
```

```
atggctctga gttcttctag gcccttctgt gtacacacat gcttatatga aggcttgagg    3360
atatagaaca catgccctgc cctgcatgtg catatagaca caatggcatg tgcataaggc    3420
atgtacatgt gcatgcacat gtgcacatac atgtagtgta ttgcattcag accaaatgag    3480
gttagatata gatcatgggt ccctggcctg gacactcatg tagccagcca ctagtgaatt    3540
tggcatgaca cctctctatc atctcagggt tggtgtgtag gttgccaggt tggtgtgggt    3600
tgccaggtga cataggtgta gctgtgagcc tctgctaatg tgaggctagt gttgagcgct    3660
tcagagaagc ctggttctaa tgctgacttc ctgttggcta ggtctaacag agggacaggc    3720
tctctaacct ggactcactc tctcatcatc tctctctctc tcctctctct ctgtctctct    3780
gtctctctgt ctctctgtct cttgccttag ttgcactctg gctattggtc ctccctcctg    3840
gtgaccaccc tgacgccagc cccttggcct ttgagaacgc tacacaccta actaaagtca    3900
tctcctacta gaagctcaga gaagggccag ccatctctca gcagatggag agttcttag     3960 aagcaccaga gctcctgaga gctgccacga gtcactccca ggaatcaccg tgaagctagg    4020
gaaatcaagg cacaaggtac gagaggctga gccacgctgg ggctctctta cctgtagaca    4080
gtgaatctcc aggaataagg cgggcagaga agcagtgctg gtcttactag ccaaaggtgg    4140
aagtggttta ggggagcgag gagggtgggc tgcctggaag atactctgga cctgaaggct    4200
tggtggaagt ggggagccag ggtagaggaa gcagacaggt gggggctcct tggggagaga    4260
gggcctagag cctaggttga gacggggct gatcagcagc tcttgcctct ggtctgactt     4320
tcaactgccc aattatccct aagtgtctcc tatcgaccga ccgcagctgg tgctgtccgg    4380
tacgtgttct gagcctacag ccccgaggct gctgctccat ccgatggcct cgttagggct    4440
aattgctctg gcatttgggc ctgatgagga caagaatggc tggaccctac cagatgtcag    4500
ggagcttcat tctctttcca gtcagattgg tgagctgtgt cagggacaaa gggccctgcg    4560
gtctcactga gcatcaggtc cctgctttac aacccatctc agtctcctgg tggcagggaa    4620
aagcaacctc actctccctt ctgtcttggg ctcaccctgc acagcactta ggcaactggt    4680
catgatgtct tgaccaactt aaatcccaga gaagctccca ctgcctttca gggtatgtca    4740
gttgatgatt tcatggacct gcatctctgt gagcaggaac actgaccca gagcccatct     4800 ggtgacagga ttcttgagac cctggcatca tgtgtttcta tagaaagcga tttgggtgga    4860
cttgtcaaag tgggtggggt atgtgtttgc gtgtgtgtgt gtggggtct ataggtatag     4920 catgtttgtg aatgcatgaa catattataa tacatgtatg cctatgcgat tctgtttgta    4980
tgtgtatatc tgtgttcgca tatgtttgtg tgtgcatgtg gctgctccta tgtatacttg    5040
tgtatgtatt tgtgtgtctg tgtctccatg tataagcact gtgaatctgt atatctgtat    5100
gtgcatatgt ttgtgtgtct atgtgtctat gtatatacca ttgtgtatat acatttgtgt    5160
gtgccaatct ctctctgaat gtatctgtat atggccatat gtgtacatgt atgtctttat    5220
acatgtgtgt atgcctatgt atgtcctcat atatgtgtgg tcatgtgtct ctgtgtgtac    5280
atgcttctgc gtgtctatgg tagaaggtca tgatgctggt tgaaagtggc ctttgagcct    5340
aggttgtaga ggcatgtgtt ccaaatgcac ataggtttcc atagtgccca agctatggg     5400 gtagatctgg ggtccttgct ccaagaccaa ggatcaggac accccctagt cctctgcctc    5460
cttagttcca tgatgtcctg ggcagggagg tccatatcag cagggtgcat acaggatagc    5520
acagcagcct ccacaccagc aacactgatg ccagggagtg ggtgagctgt cattacggac    5580
aattaagcac cgtgctgaga gagaaaggcc ccgtgtgctc cccgtctctg caggcctaat    5640
```

-continued

| | | | | |
|---|---|---|---|---|
| cgctgtggtg | acagaggagg | gtaattatca | ggacggctgt | gaatggcaca ggcattacag | 5700 |
| gggtgtaaag | ggctcaggaa | ggagggaggg | cctgctatgc | ccccagcacg catctgagcc | 5760 |
| cagagcaggc | aatggcccac | tgcactggcc | ttgcgcttca | gatcagcccc ctttcttaac | 5820 |
| tgctagggga | tgcttcccaa | tcactcctct | aggctctgcg | gcttgcttcc agcctgtacg | 5880 |
| ctgtccagag | agccttcaaa | gcctcacttc | gaccaaccag | aagcctctcg tcagccctgc | 5940 |
| cctgaccgcg | tgtgcctctt | caaagtgaga | tttagcagct | gcagctgggg gtgcctgagc | 6000 |
| cccactcatg | ctgtcttcct | tgaagacaga | agtgttggga | gctgaggacc tgggctgtat | 6060 |
| gatccagaga | agtagtgtgc | ttctgggtct | cagctctccc | ttctgtagaa tgggtctgtc | 6120 |
| tgaaatggaa | aggcaggtgc | ccctctgcag | ggcctaatct | gagtcgccat gagtggttaa | 6180 |
| aagatccagc | ttgtctgtgg | gtgagctttg | agaggaggca | gggacctcta gcatggaaca | 6240 |
| gggctgagtc | ctggaaagct | gaccaagggc | aggcctaaga | ggcctcttgg gattcttctc | 6300 |
| atcaaaaagg | gcatgggaca | cagctaaagc | gtccagggct | cctctgtgcc cacagatgcc | 6360 |
| ttagatcttg | gcacaatgta | gtcagccagc | tccgtgtgtg | tgtgtgtgtg tgtgtgtgtg | 6420 |
| tgtgtgtgtt | tgcatgtatc | tcacagacgt | agtgcacaat | ggcctggatg tgaacagagg | 6480 |
| caagagtctg | ggccagcagt | tgtctcccag | gagggtccaa | agacatcgta ttttcaagtt | 6540 |
| taggccaggt | gctcacttgg | gtgagctcag | acacagacaa | aggtctggag agcacacatt | 6600 |
| ccccaccccc | acccagcttc | tatgcaagca | cctccagccg | agacaagaaa acgaattaaa | 6660 |
| aagcaatatt | tgtgtcagcg | taagacattt | gccgaaaggt | taaatccaca ctcgtggtgc | 6720 |
| tgcacagagc | cccctgtgc | aggatttgtt | aggcacagct | ccctcctacc ccgtgccacc | 6780 |
| tgagcaaatg | ccaggctggg | tgggctgaa | ccagctgggc | ttgctcaccc tggaatcccc | 6840 |
| agcaccctcc | aaaggaggac | cctgggagtg | ggcatagacg | cccttcaggt gtgggcaaca | 6900 |
| gcccccagtc | ctcaggatga | aaggctaagg | tgcagccagc | tctgccttca cggtgggaat | 6960 |
| gtctctatgt | gagcccttc | tgggctgtga | agaacgctct | gagaagggtc ctgggaccct | 7020 |
| ggataggcca | gagctgtgct | gggcatgtag | agacaggagt | gggctaaagc agcaaaggca | 7080 |
| ctgaccaagg | aagagttcag | agaggagcgt | ggaatatggg | gaggggttca tagtaagaga | 7140 |
| gagcaggcag | tggagagtaa | atagtcactg | agccggggtt | tatggggttt gtaggagctt | 7200 |
| actcagagaa | agtagatgag | agatgccatg | ccagtctgag | tatcacagag ccccaggctc | 7260 |
| tcctgggaac | ggaactgtga | gggccagaag | gtcagcaagg | gaggttaggg agagttcctt | 7320 |
| ttgtactgac | tcagcattta | tcctgctccc | aggggcaat | ggggccagt gagggatgca | 7380 |
| gagcaaggca | gtgatgtggc | aggcagttcc | tgttgtgaaa | gagctgggaa gggagcgggc | 7440 |
| tgggcctggt | acgtacagca | gccgttctga | tggtccgagt | gctgtctaga ggtgcagtga | 7500 |
| gacttcagtg | atcatgccag | aacagaagct | aagcggggtg | gggactgcga gttcaggctt | 7560 |
| ctgggtcttg | caaatatcca | gaatgctaaa | tcctcagaac | cccagggtgg ccattttcag | 7620 |
| agtgggtttt | gtccttgg | cacttgtgca | gactccaata | tccagaggga taaggatggt | 7680 |
| actcttcagt | accttagtg | agaggacact | tttctctgaa | gggcttgaat gtgccgagcc | 7740 |
| attacctgaa | ggaaggaaat | gactccaggg | acataggatg | gcccagcac aactcacctg | 7800 |
| ctacagagaa | aggtcccctc | cctggtctcc | ttagagatcc | tgtttccctg gctgaggaag | 7860 |
| ctagggtgga | tctttgtgta | agtgggtgtg | gatgctaact | ggaaaacaaa aggtcactta | 7920 |
| ctgttagacc | tcggggtacc | atggaagaga | tgatcactga | gtgtgccctt acatggggac | 7980 |
| cagctgagaa | tggggctacc | actagctcga | gaccatgata | cagggaataa gtgtgcattt | 8040 |

-continued

```
gggggtaggg agtggctcag aatactctta accaaagcag aggtttgctc ccacaggaag    8100
gtgaggtcag aaggccttag ggagctgcca ggggctaggg ttggcaccat ctcccaggct    8160
gtgtctttaa ggagatgata atcagaggga tagaaccttg caaaagtggg ccagtcttgg    8220
gaatactata gaggaatagc cttctggaac attctgtgtc tcataggacc tgcctggatc    8280
cagccccagt gccagcacat ataccgactg gggcagtgaa tagatagtac actttgttac    8340
atgggctggg gggaacatgg cccatgtcct ggaggggact ttatgacaga catccaaaaa    8400
tccagtgaga gggcttctag atttgtctcc aaaggttata gttctaacat gagcccttag    8460
gaaatccagc atggttctcc ctgtgtgccc tggtttggtt agagagctct agcggtctcc    8520
tgtcccacag aataccagcc agccctgcc ctacgtcgtg cctcgggctg agggtgattc     8580
agaggcaggt gcctgtgaca gtggatgcaa ttagatctaa tgggacggag gcctttctcg    8640
tcgccctcgc tccatgccca cccccgcctc cctcaggcac agcaggcgtg gagaggatgc    8700
gcaggaggta ggaggtgggg gacccagagg ggctttgacg tcagcctggc ctttaaagag    8760
ggcgcctgcc tggcgagggc tgtggagaca gaactcggga ccaccagagg aattc         8815
```

TRANSGENIC ANIMAL MODEL FOR NEURODEGENERATIVE DISORDERS

The present invention relates to an animal model useful for testing potential therapeutic agents for the treatment of neurodegenerative disorders, in particular disorders associated with the presence of Lewy pathology.

Lewy pathology is a defining hallmark of degenerating neurons and/or glial cells in post mortem brain tissue of patients with neurodegenerative disorders including idiopathic Parkinson's Disease (PD), dementia with Lewy bodies (DLB), a Lewy Body variant of Alzheimer's Disease (LBVAD) and multiple system atrophies (MSA). Lewy-type changes seem central and may contribute mechanistically to dysfunction and degeneration of neurons and/or glial cells in these diseases. The characteristic appearance of Lewy pathology is known to the skilled artisan and described, e.g. in Spillantini et al., Proc. Natl. Acad. Sci. USA 95:6469–6473 (1998). Lewy pathology in neurons includes the aberrant distribution pattern, e.g. in soma and dendrites, and the finding of aggregates of the presynaptic protein α-synuclein in neurons as compared to a predominantly axonal and presynaptic localisation in normal cells. Two mutations (A53T or A30P) in the α-synuclein gene are linked to early-onset familial PD with Lewy pathology.

The lack of an experimental animal model showing neuropathological changes as observed in PD, DLB, LBVAD and MSA and reflecting underlying pathological mechanisms is a major obstacle that hampers significant advance in both basic research and drug development.

It has now surprisingly been found that features of Lewy pathology are evident in the brain of transgenic or somatic recombinant animals expressing an exogenous α-synuclein gene under the control of nervous tissue specific regulatory sequences. The animals provide a first and novel model which can be used to test neuroprotective treatments for diseases involving α-synucleinopathy.

Accordingly in a first aspect the invention provides transgenic or somatic recombinant non-human animals which exhibit α-synucleinopathy. More particularly the invention provides transgenic or somatic recombinant non-human animals expressing exogenous α-synuclein. Preferably they express exogenous α-synuclein under the control of a nervous tissue specific regulatory sequence. More preferably the transgenic or somatic recombinant non-human animals overexpress exogenous α-synuclein, e.g. express exogenous α-synuclein under the control of a regulatory sequence selected from the group comprising a Thy-1 gene-regulatory sequence or a Tyrosine Hydroxylase (TH) gene-regulatory sequence.

In a further aspect the invention provides a recombinant DNA construct comprising a poly-nucleotide encoding an α-synuclein polypeptide functionally linked to a nervous tissue specific regulatory sequence, e.g. a Thy-1- or a TH-regulatory sequence.

In a still further aspect a transgenic cell expressing exogenous α-synuclein is provided, in particular a transgenic cell comprising a recombinant DNA construct comprising a poly-nucleotide encoding an exogenous (α-synuclein polypeptide functionally linked to a nervous tissue specific regulatory sequence, and expressing said exogenous α-synuclein.

Transgenic or somatic recombinant non-human animals include animals into which a suitable construct has been introduced, and, in the case of transgenic animals, progeny of such animals still retaining said construct. Examples for useful animal lines include any animal line normally kept as laboratory animals, e.g. mouse and rat lines. Very useful mouse lines are the C57BL/6 line and B6CF1 line.

α-synucleinopathy in the animals shows several striking features of Lewy pathology as it presents itself in post mortem brain tissue of PD, LBVAD, DLB and MSA patients. Like in diseased human PD, LBVAD, DLB and MSA brains, subsets of neurons in the animals show α-synuclein-stained perikarya and Lewy-like neurites. A small subset of these cells may also stain for ubiquitin.

α-synucleinopathy may be analysed applying a panel of immuno- and histochemical techniques routinely used to assess Lewy pathology in human brain and well known in the art. The level of α-synuclein mRNA expression may be analysed e.g. by RNA blotting, S1 nuclease protection techniques and/or RT/PCR (reverse transcription and polymerase chain reaction) technology, the expression pattern of the exogenous gene in the brain may be determined by in situ hybridization, and detection of α-synuclein protein in the brain may be effected using immunoblotting (western blot analysis) and/or immunohistochemical staining techniques, and the effects of the expression may be studied by histology and immunohistology, as well as by using state-of-the-art high resolution protein technologies (e.g. proteomics) and/or high-resolution RNA expression profiling (gene chip technologies).

Typically observed heterogeneous changes involved in α-synucleinopathy include sausage-like enlargements of proximal and distal neuritic segments, thick or fine thread-like inclusions, as well as beaded or spindle-shaped neurites. For example some of the most prominently involved cell groups and/or brain regions in the Thy-1-α-synuclein transgenic or somatic recombinant non-human animals include the nucleus centralis oralis pontis, the nucleus vestibularis lateralis, the deep cerebellar nuclei, the deep aspects of the tectal plate, and motor nuclei in the spinal cord. In TH-α-synuclein transgenic or somatic recombinant non-human animals, the potentially affected and involved cell groups include mainly the catecholaminergic neurons, including those located in the substantia nigra (that are also affected in patients with PD), and that have been shown to expess a TH- or a TH-driven transgene. Involved cell groups may further include those that have been shown to express TH transiently, e.g. in mouse, the Purkinje cells in cerebellum during postnatal development days P21–28, and/or cells in other brain regions.

In affected brain areas of the transgenic or somatic recombinant non-human animals, there is astrocytic gliosis and microglial activation. Spinal roots immunostain for α-synuclein and axonal degeneration is apparent with nerve fibers showing breakdown and segmentation of their myelin sheaths into elipsoids. Skeletal muscle contains atrophic angular fibers indicating neurogenic muscular atrophy and they show loss of neuromuscular synapses. In agreement, the transgenic or somatic recombinant non-human animals show a progressive impairment of limb and motor function. Specific tests known in the art provide easy and also non-invasive read-outs for limb and motor function in animals.

α-synuclein sequences include wildtype α-synuclein, e.g. as disclosed in Maroteaux and Scheller, Brain Res. Mol. Brain Res. 11:335- (1991); Polymeropoulos et al., Science 276:2045–2047 (1997); Hong et al., Neuroreport 9:1239–1243 (1998); Genbank accession numbers L08850 (human α-synuclein); AF007758 (rat α-synuclein); and mutated (α-synuclein, e.g. an α-synuclein linked to early onset familiar PD, e.g. A53T, as disclosed in WO 98/59,050, and/or A30P, as disclosed in Krueger et al., Nature Genetics 18:106–108 (1998).

The transgenic or somatic recombinant non-human animals may be generated according to well established methods for introduction of a recombinant DNA construct allowing germ-line or somatic insertion including viral or non-viral vector-mediated gene transfer into fertilized eggs, zygotes or early embryos and/or a specific tissue (such as brain) in the adult animal, e.g. by gene transfer into embryonic stem cells, retroviral infection of early embryos or pronuclear microinjection. Further manipulation of resulting fertilized eggs, zygotes or early embryos and breeding of resulting transgenic founder animals follows established routes of breeding transgenic animals.

Recombinant DNA constructs useful in the present invention may be prepared according to procedures known in the art. For example a nervous tissue specific regulatory sequence may be identified and isolated starting from, e.g. routinely screening e.g. bacterial artificial chromosome (BAC) genomic DNA banks. A nervous tissue specific regulatory sequence is meant to be a regulatory sequence which is specifically active in nervous tissue, including, e.g. a regulatory sequence directing expression in neurons, in macroglial cells, e.g, astrocytes or oligodendrocytes, or in microglial cells. An example for a nervous tissue specific regulatory sequence are Thy-1 gene sequences; and an example for a Thy-1 regulatory sequence is a fragment obtainable from an approximately 8.1 kb mouse genomic Eco RI DNA fragment [Vidal et al. EMBO J. 9:833–840 (1990), Ingraham et al., J. Immunol. 136:1482–1489 (1986)], and comprises mouse Thy-1 promoter sequences, exon1, part of exon 2 and exon 4 and sequences 3' of the last coding-exon, e.g. as illustrated in SEQ ID NO: 11. Another example for a nervous tissue specific regulatory sequence is a modified version of these Thy-1 regulatory sequences, in which an internal SstI restriction fragment in the intron is replaced by enhancer sequences derived from the immunoglobulin heavy chain locus, as described e.g. in Texido et al. [J. Immunol. 153:3028–3042 (1994)]. Still another example for a nervous tissue specific regulatory sequence are TH-gene sequences, e.g. those comprising e.g. 9 kb of the 5' regulatory sequences in e.g. the rat tyrosine hydroxylase gene (Min et al., Mol. Brain Res. 27: 281–289 (1994)] and as e.g. illustrated in SEQ ID NO: 12. Expression of α-synucleins in astrocytes may be directed using state of the art expression cassettes containing e.g. sequences of the Glial Fibrillary Acidic Protein Gene (GFAP) [Balcare and Cowen, Nucl. Acids Res. 13:5527–5543 (1985); Mucke et al., The New Biologist 3:465–474 (1991); Mucke and Rockenstein, Transgene 1:3–9 (1993); Brenner et al., J Neuroscience 14:1030–1037 (1994); Toggas et al., Nature 367:188–193 (1994); Mohajeri et al., Eur.J. Neuroscience 8:1085–1097 (1996)]. Expression in microglial cells can be achieved using state of the art regulatory sequences derived from the human Fc gamma RI gene [Heijnen and van de Winkel, J. Hematotherapy 4:351–356 (1995); Heijnen et al., J. Clin. Invest. 97:331–338 (1996)].

By e.g. modification of sequences comprising a nervous tissue specific regulatory sequence and using state-of-the-art technology [e.g. as described by Zhang et al., Nature Genetics 20:123–128 (1998); Muyrers et al., Nucleic Acid Res. 27:1555–1557 (1999)] for inserting the α-synuclein encoding sequences in the desired location of the genomic sequences a re-combinant DNA construct is obtainable which may then be used in the preparation of transgenic or somatic recombinant non-human animals.

Transgenic cells expressing exogenous α-synuclein may be prepared by any technique known in the art, for example the recombinant DNA construct may be introduced by direct DNA microinjection, DNA transfection, viral or non-viral vectors, or the cells may be obtained from transgenic or somatic recombinant non-human animals, and cultured in vitro.

Models based on cells and animals of the invention may be used for example to identify and assess the efficacy of potential therapeutic agents in neurodegenerative diseases, particularly in diseases where α-synuclein is involved and/or Lewy-type pathology appears, more particularly in PD, DLB, LBVAD and MSA. In particular such models may be used in screening or characterization assays for detecting agents likely to modulate α-synuclein related, derived, and/or evoked pathology. The animals of the invention may be used for testing estrogens or estrogen modulators for their therapeutic potential in preventing or treating diseases with α-synucleinopathy.

Accordingly in a further aspect the invention comprises a method for testing a potential therapeutic agent for a specified condition, in particular a neurodegenerative disease, preferably PD, DLB, LBVAD or MSE, wherein a cell of the invention is used as target cell. More particularly it comprises such a method, wherein the agent is administered to a transgenic or somatic recombinant non-human animal of the invention. Moreover the invention comprises a screening or characterization assay consisting in or including such a method, as well as a screening assay kit comprising cells of the invention.

Methods for screening potential therapeutic agents using cell lines or animals are well known in the art. The cells and animals of the present invention may be used in analogous manner.

The recombinant cells may for example be incubated with the potential therapeutic agent and with antibodies recognizing α-synuclein. In methods where transgenic or somatic recombinant non-human animals themselves are used, the effects of the potential therapeutic agent may be determined by carrying out various investigations on the animals after sacrifice. Also after administration of the potential therapeutic agent, transgenic or somatic recombinant non-human animals may undergo specific testing in order to monitor, e.g. motor functions.

In a further aspect the present invention is directed to a novel modulator of α-synuclein distribution pattern and aggregation identified by a screening assay comprising incubating a cell expressing exogenous α-synuclein under the control of a nervous tissue specific regulatory sequence with the potential modulator and measuring and assessing changes.

The present invention also embodies an animal model for the identification of an indicator, which presence, absence or disregulation are hallmarks of predisposition, onset, progression, halt and/or reversal of the disease. For example, analysis of e.g. blood samples of transgenic or somatic recombinant non-human animals expressing an exogenous α-synuclein and at various stages, i.e. ages and/or stages of a manifesting Lewy-like disease process may be used to identify such indicators. The transgenic or somatic recombinant non-human animals provide a novel means to identify in single α-synuclein protein species pathological changes associated with α-synucleinopathy. This approach is also useful to detect changes in proteins other than α-synuclein. Overall, it illustrates the potential of the animal models to discover novel protein species that are specifically associated with the development of α-synucleinopathy. The novel protein species offer potential as novel drug targets for therapy, as reagents to develop novel e.g. antibodies for diagnostic purposes, and/or as surrogate markers.

Furthermore, the type of modifications that distinguishes these proteins from their normal counterparts provide links to pathways that can be exploited therapeutically in the context of α-synucleinopathy. The transgenic or somatic recombinant non-human animals provide a novel means to identify pathological changes associated with α-synucleinopathy and in single protein species, which potential can be exploited e.g. as targets for therapy or as surrogate markers. Functional changes in the animals can be recorded using some behavioural paradigms. For example, by recording altered locomotor activity in the transgenic animals as compared to their non-transgenic littermates, following an injection of low doses of cocaine (e.g. 10 mg/kg).

In accordance with the foregoing the present invention thus provides (1) A transgenic or somatic recombinant non-human animal, e.g. mammal, e.g. a rodent, e:g. a rat or a mouse, which exhibits α-synucleinopathy, e.g. a transgenic or somatic recombinant non-human animal expressing exogenous α-synuclein, e.g. a transgenic or somatic recombinant non-human animal expressing exogenous α-synuclein under the control of a nervous tissue specific regulatory sequence, e.g. expressing exogenous α-synuclein under the control of a regulatory sequence selected from the group comprising a Thy-1 regulatory sequence and a TH regulatory sequence.

(2) A transgenic or somatic recombinant non-human animal, e.g. mammal, e.g. a rodent, e.g. a rat or a mouse, comprising and expressing an exogenous polynucleotide encoding an α-synuclein polypeptide, e.g. wildtype α-synuclein or a mutated α-synuclein, e.g. an α-synuclein linked to early onset familiar PD, e.g. A53T and/or A30P, functionally linked to a nervous tissue specific regulatory sequence, e.g. a Thy-1- or a TH-regulatory sequence.

(3) A recombinant DNA construct comprising a polynucleotide encoding an α-synuclein polypeptide, e.g. wildtype α-synuclein or a mutated α-synuclein, e.g. an α-synuclein linked to early onset familiar PD, e.g. A53T and/or A30P, functionally linked to a nervous tissue specific regulatory sequence, e.g. a Thy-1- or a TH-regulatory sequence.

(4) A transgenic cell expressing exogenous α-synuclein, e.g. comprising and expressing a recombinant DNA construct as under (3).

(5) A method of producing a transgenic or somatic recombinant non-human animal as under (1) or (2) wherein said animal is generated by introducing a recombinant DNA construct as under (3) into the genome of germline or somatic cells, e.g. by viral or non-viral vector-mediated gene transfer into fertilized eggs, zygotes or early embryos and/or a specific tissue in the unborn, e.g. the embryo, or born, e.g. young or adult, animal, and breeding of resulting transgenic founder animals or maintaining resulting transgenic animals.

(6) A method for testing a potential therapeutic agent for modulating Lewy pathology wherein the agent is administered to a transgenic or somatic recombinant animal as under (1) or (2) or is contacted with a cell according to (4) and α-synuclein distribution pattern and aggregation is determined.

(7) A method for screening a compound or a combination of compounds for the ability to prevent, revert and/or stop cells from undergoing change to Lewy pathology comprising contacting a cell as under (4) or an animal as under (1) or (2) with the compound or combination of compounds and observing α-synuclein distribution pattern and aggregation.

(8) A method for screening a compound or a combination of compounds, e.g. an estrogen or an estrogen modulator, for its potential to prevent or treat a disease with α-synucleinopathy, comprising contacting an animal as under (1) or (2) with the compound or combination of compounds and comparing the results obtained in a test for motor deficits, e.g. Rotating Rod test, with treated animals vs. untreated animals, less motor deficits being indicative for a therapeutic potential.

(9) A screening or characterization assay consisting in or including a method as under (7) or (8).

(10) A screening assay kit comprising cells as under (4).

(11) A compound for use in the treatment of a neurodegenerative disease associated with the presence of Lewy pathology which has been identified by a method according to (6), (7) or (8) or by using an assay or an assay kit according to (9) or (10).

(12) A composition for preventing, reverting and/or stopping neural cells from undergoing change to Lewy pathology, which composition is effective to modulate α-synuclein distribution pattern and aggregation in neural cells.

(13) A method for treating a patient suffering from a neural condition comprising administering to the patient a pharmaceutically effective amount of a composition effective to modulate α-synuclein distribution pattern and aggregation in neural cells.

(14) A method for the identification of an endogenous indicator of predisposition, onset, progression, halt and/or reversal of human diseases associated with Lewy pathology comprising analysis of changes detectable in animals as under (1) or (2) or cells as under (4) and/or the causes thereof.

The following examples illustrate the invention without limitation.

EXAMPLE 1

Transgenic Mice Expressing a Human α-synuclein A53T and a Human α-synuclein Wild-type Transgene, Respectively, Under Control of (Mouse) Thy-1 Regulatory Sequences (a) Preparation of DNA Constructs A wild-type human α-synuclein cDNA is cloned by PCR amplification (2 min 93° C.; 3 cycles of 15 s, 93° C.; 30 s, 55° C.; 30 s, 72° C.; 2 cycles of 15 s, 93° C.; 30 s, 60° C; 30 s, 72° C; and 30 cycles: 15 s, 93° C.; 30 s, 66° C.; 30 s, 72° C.) using 20 ng human brain cDNA as template (Clontech), and two oligonucleotides SEQ ID NO:1 and SEQ ID NO:2. The PCR product (396 bp) is cloned into pMOSBlue (Amersham) and the A53T mutation is introduced by PCR (30 s, 93° C.; 14 cycles of 30 s, 93° C.; 1 min, 55° C.; 13 min 68° C.) directed mutagenesis (Stratagene) and the two oligonucleotides SEQ ID NO:3 and SEQ ID NO:4. The identity of the wild-type and mutant cDNAs is confirmed by sequencing (and compared to the sequence as described under accession number L08850 for human α-synuclein). A pUC13-based vector containing an approximately 8.1 kb size Eco RI DNA fragment comprising the mouse Thy-1.2 gene [Evans et al., PNAS USA 81: 5532–5536] is modified such that a 1.5kb BanI-XhoI fragment carrying exon 3 and flanking intervening sequences (according to the sequence of the mouse Thy1.2 gene as described in Ingraham et al., J. Immunol. 136:1482–1489) is replaced by a linker sequence encoding the unique Xho I recognition site [Moechars et al., EMBO J. 15:1265–1274 (1996)]. Intervening sequences are removed, leaving the XhoI site intact. The 2.8 kb of plasmid vector sequences are removed by NotI digestion [the α-synuclein cDNAs are contained in a modified Thy1 cassette plasmid vector. (Modification is done by inserting a linker into the PvuI site that flanks the 3' end of the Thy1 gene sequences in the original Thy1 cassette (i.e. see Lüthi et al., J. Neurosci. 17:4688–4699 (1997). The linker converts the PvuI site resulting in restriction sites for PvuI, EcoRI, and NotI, respectively)]. Mutant and wild-type aα-synuclein cDNA fragments (NdeI-SmaI) are blunted (Klenow), and inserted into the blunted XhoI site of the Thy1 cassette [Sauer et al., In: Krieglstein (ed.) Pharmacology of Cerebral Ischemia, 581–590 (1996); Lüthi et al., J. Neurosci. 17:4688–4699 (1997)] to generate Thy1αSNwt and Thy1 αSNA53T.

(b) Microinjection and Breeding

Linear NotI DNA fragments comprising transgene without plasmid vector sequences are isolated and injected into homozygous C57BL/6 mouse eggs. Genotyping is performed by PCR (using the same oligos as for cloning the α-synuclein cDNA; 5 min 95° C., 30 cycles of 30 s 95° C., 1 min 60° C., 1 min 72° C., and a final extension of 10 min at 72° C.) on column-purified (Qiagen) tail DNA.

(c) Description of Pathology in Transgenic Mice

A successful line expresses α-synuclein above endogenously expressed α-synuclein levels (and also above levels as compared to those of endogenous Thy-1 mRNA) as shown by Northern blot analysis [using isolated total brain RNA (TriZol method; 10 μg loaded per gel lane); blots are probed using either a 364 bp human α-synuclein cDNA probe (i.e. a NdeI-SmaI restriction fragment of the cloned human α-synuclein cDNA as described in (a) and encompassing the full human α-synuclein coding sequence), a 111 bp cDNA probe encompassing only the coding sequence for the 37 C-terminal amino acids of α-synuclein (this probe is generated by PCR amplification using as template the cloned 364 bp human α-synuclein cDNA as described in (a) and SEQ ID NO:5 and SEQ ID NO:6 as primers), or a 769 bp Thy-1 probe (spanning the restriction fragment from the Xho I site at position 4611 to the Bam HI site at position 5380 in the Thy1.2 gene sequence as described by Ingraham et al., J. Immunol. 136:1482–1489) and using standard procedures] and Western blot analysis [14,000×g supernatent fractions of half-brain homogenates (homogenized in 2 ml E-buffer; 50 mM Tris-HCl, pH7.4, 1% NP-40, 0.25% Na-deoxycholate, 150 mM NaCl, 1 mMEDTA, tablets containing a cocktail of protease inhibitors (Boehringer ) and left on ice for 30 min) are used; 15, 25 or 50 μg protein is loaded per lane and separated on 15% SDS-PAGE; after blotting and blocking non-specific binding, membranes are incubated with rabbit anti-α-synuclein polyclonal antibody (1: 1000; AB5038, Chemicon), followed by AP-conjugated anti-rabbit IgG (1:50.0000; Sigma AO418), and chemiluminiscent detection (Clontech)]. Abundant expression and stably transmitted transgene mRNA levels in brain correlate with a significant increase in α-synuclein protein levels in brain homogenates. Patterns of transgene expression in situ occur in subsets of neurons throughout e.g. the telencephalon, brain stem, and spinal cord. Endogenous α-synuclein mRNA expression is prominent e.g. in the telencephalon.

Lewy-like pathology appears in mice aged from 12 weeks.

(i) Lewy-like Pathology in the Transgenic Mouse Brain.

Mice aged from 12 weeks are examined applying immunohistochemical techniques routinely used to assess Lewy pathology in human brain. α-synuclein immunostaining (performed in paraffin and free-floating brain sections) reveals subsets of neurons in the telencephalon, brain stem and spinal cord, with high protein content in cell bodies and dendrites. This pattern is in sharp contrast to the protein's characteristic axonal and presynaptic distribution in the vast majority of neurons in non-transgenic mouse brain. Perikaryal and neuritic staining of neurons for α-synuclein is characteristically associated with Lewy bodies and neurites in the human. In addition, α-synuclein staining shows heterogeneous changes of neurites such as sausage-like enlargements of proximal and distal neuritic segments, thick or fine thread-like inclusions as well as beaded or spindle-shaped neurites. Such changes are most prominent and most frequently (but not exclusively) detected in subsets of neurons located in brain stem and spinal cord. Prominently involved cell groups include e.g. those in the nucleus centralis oralis pontis, the nucleus vestibularis lateralis, the deep cerebellar nuclei, the deep aspects of the tectal plate, and motor nuclei in the spinal cord. Occasionally, dystrophic neurites and cell bodies also stain intensely for ubiquitin. Ubiquitin-stained neurites display morphological features that are remarkably similar to ubiquitin-positive neurites in the brain of e.g. PD patients.-Cells with Lewy-like α-synuclein-positive features greatly outnumber those staining for ubiquitin in transgenic mouse brains that show ubiquitin-stained Lewy-like features. Also in diseased human brains ubiquitin-stained neurons represent a smaller subset of α-synuclein stained cells with Lewy pathology.

(ii) Lewy-like Pathology in the Transgenic Mouse Spinal Cord, Motor Nerves and Muscle.

Approximately 80% of the motor neurons in the anterior horns of the spinal cord also express the transgene. Specific to the transgenic mice, many of these cells show perikaryal α-synuclein staining, some also reveal Lewy-like pathology, pronounced ubiquitin immunoreactivity, and staining when silver-impregnated according to the Campbell-Switzer pyridine silver technique [Campbell et al., Soc. Neurosci. Abstr. 13:678 (1987)]. Anti-GFAP and anti-phosphotyrosine antibody staining in transgenic spinal cord shows, and likewise in other brain regions with Lewy-like changes, evidence for astrocytic gliosis and reactive microglia, respectively, that is specific to the transgenic tissue as compared to non-transgenic untreated littermate mice. In longitudinal sections of a spinal root α-synuclein immunoreactive nerve fibers are seen that are specific to the transgenic mice. Using Luxol-Holmes staining [Holmes, Anat. Rec. 86:157–187 (1943)] of spinal root sections, axonal degeneration with breakdown and segmentation of myelin into ellipsoids is apparent. In cross-sectioned bundles of nerve fibers within muscle, strongly α-synuclein immunoreactive axons can be seen. When cross-sectioned and Luxol-Holmes stained, muscle fiber bundles show atrophic angular fibers indicating neurogenic muscle atrophy.

(iii) Motor Deficits

Motor deficits appear early-on (>3–4 weeks of age) and these progressively worsen. The early onset of motor symptoms is easily detected using the art of the Rotating Rod paradigm in which the performance of the animal is measured (in seconds) to stay on a rotating rod at a speed of e.g. 36 rpm. Furthermore, motor deficits are detectable by simply placing the animal (aged 4–10 weeks) on a grid e.g. a cage top with grid beams (2–3 mm thick) and about 0.8–1.0 cm apart. Transgenic animals limb dysfunction that is particularly evident in the hind limbs. Unlike non-transgenic mice, the transgenic mice show a greatly decreased capability to maintain their hind limbs and feet on the beams of the grid. Very frequently, their hind limbs simply slide off the beams.

(iv) Identification of Novel α-synuclein Protein Species in Transgenic Mouse Brain Transgenic and wild-type mouse brains of e.g. line 9813 are homogenized in 4 volumes of buffer-1 (7 M Urea, 2 M thio-urea, 4% CHAPS, 1% DTT, 1 tablet with a coktail of protease inhibitors (Boehringer Cat, No. 1836153) and 2.5% Pharmalyte 3–10 (Amersham, Cat. No. 17-0156-01), and centrifuged at 13.000×g. The supernatant is used for an isoelectric focusing (IEF; e.g. 32 hr, 90.000 V) analysis using e.g. an 18 cm strip, pH 4.5–5.4 (Pharmacia, Cat. No. 90-1000-96; preincubated over night in 130 microliter sample plus 270 microliter buffer-1). Subsequently, the IEF strip is equilibrated in a solution containing DTT followed by an equilibration in a solution containing iodoacetamide, and electrophoresis in the second dimension in a 12% acrylamide gel. After electrophoresis, the gels are either stained with coomassie blue to visualize proteins, or electroblotting is performed and the proteins transferred onto PVDF membrane (electrotransfer buffer is 20% methanol in TrisGlycine; 32 V constant voltage; 90 min at 4° C.). Following the transfer, the membrane is either stained with SyproRuby or incubated with antibody. The latter is performed as follows: to block nonspecific binding, the membrane is incubated in 1% non-fat milkpowder in PBS with 0.01% Tween for 1 h, followed by an incubation in a solution with an α-synuclein antibody e.g. AB5038-50UL (Chemicon), diluted 1:3000 in 1% Milkpowder in PBS-0.01% Tween for 1.5–3 h, washing 3 times 10 min. in PBS-0.01% Tween, incubation for 1 h in 1% Milkpowder in PBS—0.01%Tween containing an anti rabbit lg (e.g. Amersham, 145659; G1i2000), washing 3×10 min. in 1% Milkpowder in PBS—0.01% Tween, covered with ECL solution, and exposed to film. These analysis reveal novel α-synuclein protein species (more basic as well as more acidic species) that are not present in wild-type mouse brains or in human brains from normal individuals. Their corresponding protein spots are isolated from the 2D gels, digested with e.g. trypsin, and analysed by MS.

EXAMPLE 2

Transgenic Mice Expressing a Human α-synucleinA53T and a Human α-synuclein Wild-type Transgene Under Control of (Rat) Tyrosine Hydroxylase Gene Regulatory Sequences (a) Preparation of DNA Construct To generate the two $TH_{9kb}$-α-synuclein-$A_{n/sv40}$ constructs, mutant and wild type α-synuclein cDNA fragments are excised from their vector using Ndel-Smal, blunted using the Klenow reaction, and cloned into the blunted EcoRI site of $TH_{9kb}$-$A_{n/sv40}$. The latter cassette is produced as follows: (i) a 0.8 kb $A_{n/sv40}$ BglII-BamHI fragment is excised from a pSV2-type (dhfr)-vector (Mulligan, R. C & Berg, P. 1981. PNAS USA 78: 2072–2076) and cloned into the BamHI site of pPolyIII-I (Lathe, R., Villotte, J. L. & Clark, A. J., 1987 Gene 57: 193–201.), (ii) the 9 kb HindIII-EcoRI TH promoter fragment is isolated from its original plasmid (Min, N., Joh, T. H., Kim, K. S., Peng, C. & Son, J. H. 1994 Molecular Brain Research 27: 281–289) and cloned directionally into the EcoRi-HindIII sites of pPolyIII-II/$A_{n/sv40}$, (iii) the blunted Ndel-Smal cDNA fragments encoding the wild type and mutant synuclein, respectively, are separately cloned into the blunted EcoRI site of pPolyIII-I/$TH_{9kb}$/$A_{n/sv40}$.

(b) Microinjection and Breeding

Linear NotI DNA fragments comprising transgene without plasmid vector sequences are isolated and microinjected into fertilized eggs of C57BL6 mice and all the transgenics are generated on this inbred background.

Tail DNA is column purified (Qiagen) according to the manufacturer's protocol. PCR genotyping is performed using 200–400 ng genomic DNA, a TH-specific forward primer SEQ ID NO:7 and a human synuclein-specific reverse primer SEQ ID NO:8. This yields a 600 bp transgene-specific DNA product. PCR cycles are 5' 95° C.; 30 rounds of 30 s 95° C., 1 min. 60° C., and 1 min. 72° C.; 10 min. 72° C. Standard molecular methods are used for these and other (see below) DNA analysis.

(c) Description of Pathology in Transgenic Mice

A successful line expresses α-synuclein at high levels (i.e. as compared to endogenous α-synuclein mRNA levels in situ). At least one line for each of the respective TH-human α-synuclein (i.e. wild-type and A53T mutant) expresses the transgene in catecholaminergic neurons including the vast majority of dopaminergic neurons in e.g. the substantia nigra pars compacta and the ventral tegmental area. The development of α-synucleinopathy is assessed in the relevant brain regions (i.e. those where the cell bodies of the TH-driven transgene expressing cells are located including the substantia nigra, ventral tegmental area, locus coeruleus, olfactory bulb, and few but very distinct cells located in the deeper layers of the cerebral cortex). Typical pathological changes that are seen include somatic and dendritic accumulations of human α-synuclein, and (dystrophic) neuritic changes similar to those described in Example 1. Changes in the integrity of transgene expressing catecholaminergic neurons, their axons, and/or their terminals are also visualized using immunohistological stains that detect some of a variety of antigens including but not only tyrosine hydroxylase(TH), the vesicular monoamine transporter-2 (VMAT-2), the plasma membrane dopamine transporter (DAT), dopamine beta-hydroxylase (DBH), the norepinephrine transporter (NET), and/or EphB1 (an Eph family receptor tyrosine kinase that is differentially expressed in ventral mesencephalic neurons [Yue et al., J Neuroscience 19:2090–2101 (1999)]. Dendritic changes in subsets of these cells can be monitored using, in addition to the human α-synuclein specific antibody LB509, antibodies against e.g. MAP2 and β-tubulin. Changes can also be seen using immunohistological methods that detect antigens in or on cells in catecholaminergic neurons projection fields. For example, when using some of a large panel of antibodies that define different subsets and/or cell types in the striatum where most of the different cell types have been identified using antibodies against e.g. Leu- and Met-enkephalin (Enk), substance P (SP), choline acetyltransferase (ChAT), somatostatin (Sst), parvalbumin (PV), calretinin (CR), calbindin (CB), L-amino acid decarboxylase (AADC), dopamine- and cAMP regulated phosphoprotein,(DARPP-32), adenosine $A_{2A}$ receptor ($A_{2A}$ R), muscarinic acetylcholine receptor m4 (mAChR4). Pathological changes can also be detected at the ultrastructural level by immuno- and conventional electron microscopy as described in Example 1, and using, in addition to antibodies for α-synuclein, antibodies directed e.g. against DAT or other antigens present in dopaminergic terminals in the striatum. Additional changes can be detected using protein chip technology (see Ciphergen's SELDI™ procedure), combined with mass spectrometry (MS). For example, 8 weeks old transgenic (TH9kb-human-α-synuclein A53T) and control mice are sacrificed by cervical dislocation. Striata of both hemispheres are quickly dissected out and processed seperately from the remainder of the brains. The tissues are homogenized in 500 μl(striatum) and 2 ml (remainder of the brain) extraction buffer (50 mM Tris-HCl, pH7.4, 1% NP-40, 0.25% Na-deoxycholate, 150 mM NaCl, 1 mM EDTA, and a tablet (Boehringer Mannheim, Germany) with a cocktail of protease inhibitors), left on ice for 30 min.,and centrifuged at 14.000×g. Supernatant fractions are used at a concentration of 1 mg/ml. For protein profiling these extracts are diluted 1:10 and applied to the strong anion exchange protein chips (SAX2, Ciphergen) following the Ciphergen-procedure including washing in chip-specific wash-buffer at pH 8.5. The analysis of these protein-chips shows downregulation of a protein of approximately 33 kDa in total brain, as well as an upregulation of a protein of approximately 6–7 kDa only in striatum. The corresponding proteins are also isolated from 2D-gels (as described in Example 1) and used for analysis by MS.

EXAMPLE 3

Transgenic Mice Expressing a Mouse Wild-type α-synuclein Under Control of (Mouse) Thy-1 Regulatory Sequences C57BL/6 mouse α-synuclein (wild-type) cDNA is cloned by PCR amplification in analogy to Example 1 using oligonucleotides having nucleotide sequences as illustrated in SEQ ID NO:9 and SEQ ID NO:10, respectively. PCR amplification reactions are performed using High Fidelity Taq polymerase in the buffer supplied with the enzyme (Boehringer) in a 50 μl final volume with approximately 20 ng cDNA and the two oligonucleotides. The following conditions are used: denaturation at 94° C. for 1 min, 35 cycles of denaturation at 94° C. for 10 sec, annealing at 58° C. for 30 sec, and extension at 72° C. for 1.5 min, then 72° C. for 3 min The PCR product is identified by TBE/agarose gel electrophoresis, excised from the gel and cloned into pGEM-T-Easy (Promega). Two clones, differing only in their orientation relative to T7 and Sp6 polymerase promoter sites are selected and the identity of the insert to the mouse α-synuclein cDNA is confirmed by sequencing following standard methods. Subsequently, the mouse α-synuclein cDNA is excised using NotI, blunted, and inserted into the blunted XhoI site of the Thy1 cassette (as described in Example 1). DNA microinjection of the vector-free transgene, breeding of the mice, and subsequent analysis are as described in Example 1, and using anti-α-synuclein antibodies that recognize mouse α-synuclein.

EXAMPLE 4

Transgenic Mice Expressing Mouse Wild-type α-synuclein Under Control of (Rat) Tyrosine Hydroxylase Gene Regulatory Sequences The mice are constructed, bred and analyzed as described in Example 2 but using the mouse α-synuclein-encoding cDNA (as described in Example 3) inserted into the TH-cassette.

EXAMPLE 5

Transgenic Mice Expressing Mouse Wild-type, Human Wild-type, and Human Mutant (A53T or A30P) α-synuclein, Respectively, Under Control of (Rat) Tyrosine Hydroxylase Gene Regulatory Sequences and (Mouse) Thy-1-gene Derived Sequences The transgenes are constructed as follows: The above described Thy-1 cassettes carrying either one of the human or a mouse α-synuclein cDNA are cut by BstEII and PvuI to remove the Thy-1 promoter sequence, and the rest of the chimeric Thy-1exon1a/b-Thy-1exon2/synucleincDNA/Thy-1exon4-Thy-1-end fragment is isolated. pPolyII-II/TH$_{9kb}$/A$_{n/sv40}$ is cut by HindIII and EcoRI and the 9 kb TH promoter fragment is subcloned into pPolyIII-I (after cutting with HindIII-EcoRI) lacking the SV40 polyA signal sequence. pPolyIII-I/TH$_{9kb}$ is linearized using EcoRI, blunted and the blunted BstEII-PvuI is then cloned into the blunted EcoRi site and tested for proper orientation. Finally, NotI cleavage and gel purification is used to free the TH$_{9kb}$-α-synuclein-A$_{n/Thy1}$ transgene from plasmid vector sequences before DNA microinjection into fertilized mouse, eggs. These mice are bred and analyzed as described in Examples 2 and 4.

EXAMPLE 6

Motor Deficits in Transgenic Mice Expressing α-synuclein Under Control of (Mouse) Thy-1 Regulatory Sequences Four groups of mice are formed: group 1 with male wild-type mice, group 2 with male (mouse)Thy-1-human-α-synucleinA53T transgenic mice (of Example 1), group 3 with ovarectomized female wild-type mice, and group 4 with ovarectomized female (mouse)Thy-1-human-α-synucleinA53T transgenic mice (of Example 1). The mice are trained twice daily and on two successive days to stay on a rotating rod (TSE, Bad Homburg, Germany) for 150 seconds (speed 12 rpm). Subsequently, the animals are tested on the rotarod once weekly, three times and at three different speeds (i.e., 12 rpm, 24 rpm, and 36 rpm). The cut-off time used for measuring the endurance performance in all these experiments is 60 seconds. The plotted mean endurance performance on a particular test day is the mean of the three performances at the given speed. Statistical evaluation of the data uses repeated measures ANOVA. Female mice of two independent Thy1 human α-synucleinA53T transgenic lines perform better than their male counterparts throughout most of the test period (monitoring starts at 40 days of age and ends, e.g., at 6 months of age).

What is claimed is:

1. A transgenic mouse whose genome comprises an α-synuclein transgene, the transgene comprising a nervous tissue specific regulatory sequence operably linked to a DNA sequence encoding an α-synuclein polypeptide, wherein expression of the transgene results in a transgenic mouse exhibiting a phenotype of α-synucleinopathy.

2. The mouse of claim 1 wherein the nervous tissue specific regulatory sequence is selected from the group consisting of a Thy-1 regulatory sequence and a Tyrosine Hydroxylase (TH) regulatory sequence.

3. The mouse of claim 1 wherein the α-synuclein polypeptide is a wildtype α-synuclein, an A53T α-synuclein mutant or an A30P α-synuclein mutant.

4. Progeny of the mouse of claim 1, wherein the genome of the progeny comprises an α-synuclein transgene, the transgene comprising a nervous tissue specific regulatory sequence operably linked to a DNA sequence encoding an α-synuclein polypeptide, wherein expression of the transgene results in a transgenic mouse exhibiting a phenotype of α-synucleinopathy.

5. Progeny of the mouse of claim 4, wherein the α-synuclein polypeptide is a wildtype α-synuclein, an A53T α-synuclein mutant or an A30P α-synuclein mutant.

6. Progeny of the mouse of claim 5, wherein the nervous tissue specific regulatory sequence is selected from the group consisting of Thy-1 regulatory sequence and Tyrosine Hydroxylase (TH) regulatory sequence.

7. A method of producing a transgenic mouse that exhibits a phenotype of α-synucleinopathy comprising:
   a) introducing an α-synuclein transgene into a fertilized egg or an embryo of a mouse, the transgene comprising a nervous tissue specific regulatory sequence operably linked to a DNA sequence encoding an α-synuclein polypeptide;
   b) transferring the egg or embryo comprising the transgene to a surrogate mother mouse; and
   c) allowing the transferred egg or embryo comprising the α-synuclein transgene to develop to term to produce a transgenic mouse whose genome comprises a DNA sequence encoding an α-synuclein polypeptide, wherein expression of the transgene results in the transgenic mouse exhibiting a phenotype of α-synucleinopathy.

8. The method of claim 7, which further comprises breeding of the transgenic mouse to provide progeny of the transgenic mouse, wherein the genome of the progeny comprises an α-synuclein transgene, the transgene comprising a nervous tissue specific regulatory sequence operably linked to a DNA sequence encoding an α-synuclein polypeptide, and wherein expression of the transgene results in a transgenic mouse exhibiting a phenotype of α-synucleinopathy.

9. A method for testing a potential therapeutic agent for modulating Lewy pathology wherein the agent is administered to the transgenic mouse of claim 1 and the α-synuclein distribution pattern and aggregation is determined.

10. A method for testing a potential therapeutic agent for modulating Lewy pathology wherein the agent is contacted with the transgenic cell of claim 1 and the α-synuclein distribution pattern and aggregation is determined.

11. A method for screening a compound or combination of compounds for the ability to prevent, revert and/or stop cells from undergoing change to Lewy pathology comprising contacting the transgenic cell of claim 1 with the compound or combination of compounds and observing α-synuclein distribution pattern and aggregation.

12. A method for screening a compound or combination of compounds for the ability to prevent, revert and/or stop cells from undergoing change to Lewy pathology comprising contacting the transgenic mouse of claim 1 with the compound or combination of compounds and observing α-synuclein distribution pattern and aggregation.

13. A method for screening a compound or a combination of compounds for the potential to prevent or treat a disease with α-synucleinopathy, comprising contacting the transgenic mouse of claim 1 with the compound or combination of compounds and comparing the results obtained in a test for motor deficits with treated mice versus untreated mice, less motor deficits being indicative for a therapeutic potential.

14. A screening assay kit comprising transgenic cells of claim 11 expressing exogenous α-synuclein.

15. A recombinant DNA construct comprising a nucleic acid encoding an α-synuclein polypeptide operably linked to a Tyrosine Hydroxylase (TH) regulatory sequence.

16. The DNA construct of claim 15, wherein the α-synuclein polypeptide is a wildtype α-synuclein, an A53T α-synuclein mutant or an A30P α-synuclein mutant.

17. A transgenic eucaryotic cell comprising and expressing an exogenous polynucleotide encoding an α-synuclein polypeptide operably linked to a Tyrosine Hydroxylase (TH) regulatory sequence.

* * * * *